United States Patent [19]  [11] 4,360,515
Buck  [45] Nov. 23, 1982

[54] SULFONATED ALKOXYNAPHTHALENES AS DENTAL PLAQUE BARRIERS

[75] Inventor: Carl J. Buck, Berkeley Heights, N.J.

[73] Assignee: Johnson & Johnson Products, Inc., New Brunswick, N.J.

[21] Appl. No.: 172,489

[22] Filed: Jul. 25, 1980

[51] Int. Cl.³ .................. A61K 7/16; A61K 7/22; A61K 31/315; C07C 143/24
[52] U.S. Cl. ........................... 424/56; 424/54; 424/289; 424/315; 424/316; 260/505 C
[58] Field of Search ................... 424/48–56, 424/78, 315, 289; 260/512 R, 505 R, 505 C

[56] References Cited

U.S. PATENT DOCUMENTS

| | | | |
|---|---|---|---|
| 2,215,457 | 9/1940 | Andersen | 424/56 |
| 3,282,779 | 11/1966 | Pensack et al. | 424/315 |
| 3,812,178 | 5/1974 | Weedon | 260/512 |
| 3,836,484 | 9/1974 | Danzik et al. | 260/505 R |
| 4,150,112 | 4/1979 | Wagenknecht et al. | 424/48 |

FOREIGN PATENT DOCUMENTS

| | | | |
|---|---|---|---|
| 47-38967 | 2/1972 | Japan | 424/315 |
| 322193 | 11/1929 | United Kingdom | 424/315 |
| 1296952 | 11/1972 | United Kingdom | . |
| 1507772 | 4/1978 | United Kingdom | . |

Primary Examiner—Douglas W. Robinson

[57] ABSTRACT

Compounds useful in compositions and methods for preventing the attachment of dental plaque to the surfaces of the teeth of mammals comprise certain sulfonated alkoxynaphthalenes and the pharmaceutically acceptable salts thereof. They are used in pharmaceutically acceptable vehicles that are periodically applied to teeth.

6 Claims, No Drawings

SULFONATED ALKOXYNAPHTHALENES AS DENTAL PLAQUE BARRIERS

TECHNICAL FIELD

This invention relates to certain sulfonated aromatic compounds, oral hygiene compositions comprising the compounds and to methods using such compositions to prevent attachment of bacteria to teeth. More particularly it relates to certain sulfonated alkoxynaphthalenes that have been found useful in inhibiting the agglutination of oral microbes on teeth.

BACKGROUND ART

The prevention of the deposition of dental plaque on teeth is a highly desired result. Dental plaque results when cariogenic bacteria aggregate in colonies on the surface of teeth and form a tenacious deposit thereon. The presence of plaque on teeth is believed to be a precursor to development of gingivitis, dental caries and periodontal disease.

While many attempts have been made to control the effects of cariogenic bacteria and the dental plaque they produce, for example, by fluoride, flossing, brushing, etc., treatments, these are typically directed to either counteracting the secondary effects of plaque on the teeth and gums, or to the removal of plaque that is already formed on and adhering to the teeth and surrounding tissue. Such treatments are not, however, entirely successful, and must be supplemented with periodic treatment by dental professionals. To date, there is no commercially feasible home treatment method for preventing the formation of plaque or its adhesion to teeth.

THE INVENTION

Hydrophilic sulfonic acid salt derivatives of certain alkoxynaphthalene compounds have been synthesized and found to inhibit the deposition of dental plaque onto human teeth. These alkoxynaphthalene sulfonates are substantially soluble in water or water/organic solvent vehicles and are applied to teeth from various dentifrice formulations, mouth rinses, or other oral hygiene procedures. While the mechanism of action of these sulfonated compounds in retarding plaque deposition is not known with absolute certainty, it is presumed that films of the anionically charged compounds are deposited on teeth. A mutual repulsion effect is thought to arise between the negatively charged microorganisms responsible for plaque generation and the negatively charged films of alkoxynaphthalene sulfonates. The alkoxynaphthalene sulfonates of this invention are especially effective as components of dentifrices and other oral hygiene preparations in reducing dental plaque deposition on teeth.

A particular feature of the alkoxynaphthalene sulfonates of this invention, which appears to govern their effectiveness as agents for the reduction of plaque deposition, is the balance between the hydrophobic and hydrophilic properties of these compounds. The hydrophobic groups in the alkoxynaphthalene sulfonates are the naphthalene ring and the substituent alkoxy groups. The sulfonate group is the hydrophilic moiety. Accordingly, it has been found expedient to adjust the hydrophobic/hydrophilic balance in the alkoxynaphthalene sulfonates of this invention by independently varying both the size and number of the alkoxy groups and the number of sulfonate groups.

The sulfonated derivatives which are useful for dental plaque control in accordance with the present invention are monoalkoxynaphthalene sulfonic acids and dialkoxynaphthalene sulfonic acids, and salts thereof, having a structure selected from the group consisting of structure (A),

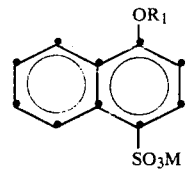

structure (B),

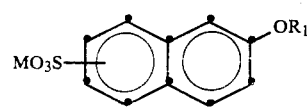

and structure (C),

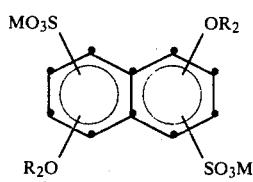

wherein $R_1$ is a linear or branched alkyl having 6 to 20 carbon atoms, $R_2$ is a linear or branched alkyl having 8 to 20 carbon atoms, and M is selected from the group consisting of hydrogen, lithium, sodium, potassium, calcium, magnesium, zinc, aluminum, ammonium and the substituted ammonium ions derived from pharmaceutically acceptable organic amines.

Due to the relatively high acidity of the free acids (wherein M is hydrogen) it is preferred that they be converted to the less acidic salts for use in the oral hygiene compositions of this invention.

The sulfonated monoalkoxynaphthalenes and dialkoxynaphthalenes of this invention can be synthesized readily by a process consisting of (1) reaction of an alkali metal salt of 1-naphthol, 2-naphthol, or a dihydroxynaphthalene with at least a stoichiometric quantity of an alkyl halide, $R_1X$ or $R_2X$ (wherein $R_1$ and $R_2$ are as defined above) to afford the mono- and di-alkoxynaphthalenes of general structures (D) and (E), followed by (2) aromatic sulfonation to the sulfonic acids of structures (F) and (G). To obtain the salts of the sulfonated alkoxynaphthalenes of this invention, the sulfonic acids of structures (F) and (G) are converted to the desired metal, ammonium, or substituted ammonium salts by neutralization and/or ion-exchange reactions known in the art. The general synthetic sequence for preparation of the disulfonic acid derivatives is shown schematically in equations (1) and (2):

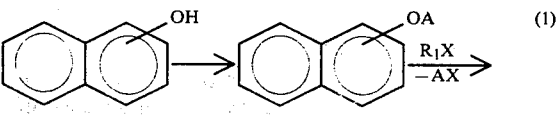

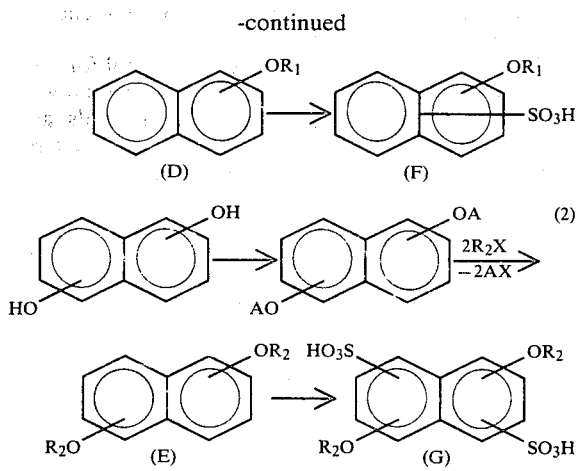

-continued wherein
A = sodium or potassium
X = chlorine, bromine, or iodine

The 1-naphthol, 2-naphthol, the various dihydroxynaphthalenes, and the alkyl halides used as starting materials in the synthesis of the monoalkoxy- and dialkoxynaphthalene intermediates are either readily available as items of commerce or synthesized by methods well known to those skilled in the art.

Sulfonation of the alkoxynaphthalenes of general structures (D) and (E) can be effected with concentrated sulfuric acid, oleum, chlorosulfonic acid and liquid sulfur trioxide. The sulfonations are generally effected in inert solvents, such as methylene chloride, chloroform, and 1,2-dichloroethane; at temperatures of 40° C. or below; and using sufficient sulfonation agent to obtain the desired mono- or di- sulfonated derivative. The preferred sulfonation agents are chlorosulfonic acid and liquid sulfur trioxide.

The position of the sulfonic acid groups on the naphthalene ring, obtained by sulfonation of the alkoxynaphthalenes of structures (D) and (E), is influenced largely by the position of the alkoxy substituents on the ring. For example, when the alkoxy group is in the alpha-position on the ring, sulfonation occurs preferentially in the position para- to the alkoxy group. When the alkoxy group is in the beta-position, the position of sulfonation is more random and appears to take place chiefly in the 6- or 7-position of the adjoining aromatic ring. When one or both alkoxy groups in a dialkoxy naphthalene are in the beta-position, the position of sulfonation is highly random. In any event the exact positions of the alkoxy and sulfonate groups is of little significance in the practice of this invention.

As previously mentioned, the more important factor governing the activity of the sulfonated alkoxynaphthalenes of this invention as agents for the control of dental plaque deposition is thought to be the balance between the hydrophobic and hydrophilic properties of these compounds. This balance can be adjusted by varying the number and size of the alkoxy groups as well as the number of sulfonate groups.

The structures of the sulfonic acid and sulfonate salt compounds of this invention can be characterized by a number of known methods: (1) NMR and IR spectroscopic analysis, (2) acidimetric assays (on the sulfonic acid derivatives), (3) metal salt analysis via atomic absorption, and (4) elemental analysis.

The alkali metal salts of the sulfonated alkoxynaphthalenes are conveniently prepared by neutralization of a water or alcohol solution of the sulfonic acid derivative with alkali metal hydroxide solutions to the potentiometric endpoint. The salts are recovered by filtration, solvent stripping, or freeze drying, depending on the type of solvent used and whether the salt precipitates directly from the solvent medium. Alternatively, sulfonate salts can be prepared by addition of at least stoichiometric quantities of an alkali metal oxide, carbonate, acetate, chloride, nitrate, or sulfate to the sulfonic acid derivative. The salts either precipitate directly, or are isolated by solvent stripping.

Multivalent metal salts, such as the calcium, magnesium, zinc, and aluminum salts, of the sulfonated products are prepared by methods similar to those described above. In an alternate procedure, multivalent metal salts can be prepared by an ion-exchange reaction between the multivalent ion and either the free sulfonic acid or an alkali metal sulfonate derivative. Ammonium salts of the sulfonic acid derivatives can be prepared by direct addition of ammonia or a primary, secondary, or tertiary organic amine.

The hydrophilic sulfonates of this invention are highly effective in reducing the deposition of plaque during in vitro testing when a suitable balance of hydrophobic and hydrophilic properties is provided in accordance with the foregoing definitions of the compounds of this invention.

Examples illustrating the effect of the hydrophobic/hydrophilic balance on the plaque barrier properties of the alkoxynaphthalene sulfonates are found in Table 1.

The in vitro test procedure employed for determining the plaque barrier activity of the test materials begins with growth of plaque in small jars containing sterilized trypticase media that has been supplemented with sucrose. Typically, ten jars are individually inoculated with 0.5 ml of unpooled freshly collected human plaque from 10 subjects. In a control series, a presterilized glass slide or an extracted human tooth is inserted into each jar. In the test series, the tooth or glass slide is pretreated with a 1% solution of the test compound (dissolved in water or other vehicle), allowed to dry in order to deposit a thin film of the compound on the surface, and the glass slide or tooth placed in the growth media. The jars are incubated under anaerobic conditions for two days at 37° C. The tooth or glass slide is removed, air dried, and stained with 0.15% FD and C and 3 red dye solution to reveal the accumulated plaque deposits. The tooth or glass slide is scored for plaque density on a 0 to 5 scale. Plaque barrier activity is reported as the % of average plaque reduction, as compared to appropriate controls for ten subjects.

TABLE 1

Plaque Barrier Properties of Alkoxynaphthalene Sulfonates

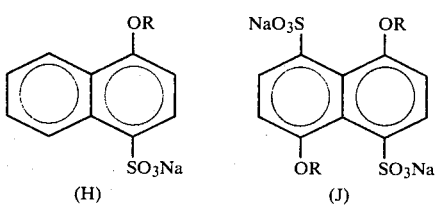

| Type Structure | R | % Plaque Reduction |
|---|---|---|
| H | $-(CH_2)_8CH_3$ | 77 |
| H | $-(CH_2)_{17}CH_3$ | 0 |
| J | $-(CH_2)_8CH_3$ | 39 |

TABLE 1-continued

Plaque Barrier Properties of Alkoxynaphthalene Sulfonates

| Type Structure | R | % Plaque Reduction |
|---|---|---|
| J | —(CH$_2$)$_{11}$CH$_3$ | 98 |
| J | —(CH$_2$)$_{17}$CH$_3$ | 23 |

EXAMPLE 1

1-Nonyloxynaphthalene

A solution of sodium ethoxide was prepared by the addition of 41. g (0.18 gram-atoms) sodium metal to 75 ml. absolute ethanol. A solution of 26.0 g (0.180 mole) 1-naphthol in 50 ml. ethanol was added, the solution heated to reflux, and 31.1 g (0.150 mole) 1-bromononane added over 80 minutes. After heating another 16 hours, the mixture was diluted with 150 ml. hot water, cooled to room temperature, and the product extracted into chloroform. The extract was washed with 2×100 ml. water, dried over magnesium sulfate, and solvent stripped to give 40.5 g of the crude product. Distillation gave two fractions of purified 1-nonyloxynaphthalene: 30.8 g, b.p. 152°–154° C. (0.1 mm) and 3.2 g, b.p. 154°–160° C. (0.1 mm).

EXAMPLE 2

Sodium 1-nonyloxy-4-naphthalene sulfonate

A solution of 7.0 g (0.06 mole) chlorosulfonic acid in 20 ml. chloroform was added with stirring, under nitrogen, at 22°–23° C. over 45 minutes to a solution of 13.5 g (0.05 mole) 1-nonyloxynaphthalene (Example 1) in 135 ml. dry chloroform. After stirring at room temperature for 16 hours, the dark green solution was solvent stripped to a syrupy residue (19.2 g) which was dissolved in 300 ml. ethyl acetate, extracted with water, the resultant emulsion partially broken by addition of some methanol, and the organic phase solvent stripped to give 5.7 g of the sulfonic acid product. The latter was dissolved in 50 ml. methanol and the solution, which had an initial pH of 2.1, neutralized with methanolic sodium hydroxide solution. The neutralized solution was solvent stripped to afford 2.7 g of sodium 1-nonyloxynaphthalene-4-sulfonate, a pale yellow solid.

Additional quantities of the salt were obtained by neutralization (with sodium hydroxide) of the water washes of the ethyl acetate extract which afforded the 5.7 g of sulfonic acid intermediate. The sodium sulfonate precipitated directly from the alkaline aqueous solution as white solids and was collected to give 1.0 g, mp 260°–265° C., and 1.9 g, mp 270°–275° C., of salt. Recrystallization from 95% ethanol gave white crystals of pure compound, mp 272°–275° C. The NMR and IR spectra were in excellent agreement with the proposed structure of the product.

EXAMPLE 3

1,5-Bis (dodecyloxy) naphthalene

To a stirred solution of 16.0 g (0.100 mole) 1,5-dihydroxynaphthalene in 80 ml. N,N-dimethylformamide (DMF) was added 16.0 g (0.200 mole) 50% aqueous sodium hydroxide, followed by 49.8 g (0.200 mole) 1-bromododecane, which was added over about one hour at 37°–54° C. The suspension was heated to about 100° C. and maintained thus for one hour. The thick suspension of solids was cooled to 40° C., suction filtered, and the dark solids washed with DMF, 95% ethanol, and chloroform. Recrystallization of the solids from ethyl acetate gave 21.9 g of the product, a green powder, mp 91°–92° C. Recrystallization afforded 21.4 g of pure 1,5-bis (dodecyloxy) naphthalene, mp 92°–93° C.

EXAMPLE 4

Disodium 1,5-bis (dodecyloxy) naphthalene-4,8-disulfonate

A solution of 3.0 g (0.025 mole) chlorosulfonic acid in 10 ml. chloroform was added over 17 minutes at 25°–27° C. to a stirred suspension of 5.0 g (0.010 mole) 1,5-bis (dodecyloxy) naphthalene (from Example 3) in 50 ml. chloroform. The resultant dark solution was stirred at room temperature for about 24 hours, during which time solids slowly deposited from the solution. The solids were filtered and washed with chloroform. The yield of the disulfonic acid intermediate, mp 135°–145° C., was 1.2 g.

A solution of 1.2088 g of 1,5-bis (dodecyloxy) naphthalene-4,8-disulfonic acid in 25 ml. methanol was neutralized from pH 0.7 to pH 8.8 with 7.1 ml. 0.524 N methanolic sodium hydroxide solution. The titer was in excellent agreement with the proposed disulfonic acid structure. Removal of solvent from the neutralized solution gave 1.2 g of disodium 1,5-bis (dodecyloxy) naphthalene-4,8-disulfonate, mp 202°–210° C.

EXAMPLE 5

Sodium 2-Nonyloxynaphthalene Sulfonate

In a manner analogous to Examples 1 and 2, 2-nonyloxynaphthalene can be prepared from 2-naphthol and 1-bromododecane and sulfonated with liquid sulfur trioxide to afford sodium 2-nonyloxynaphthalene sulfonate.

EXAMPLE 6

Disodium 2,6-Bis (nonyloxy) naphthalene disulfonate

In a manner similar to Example 3, 2,6-bis (nonyloxy) naphthalene is prepared from 2,6-dihydroxynaphthalene and 1-bromononane and then sulfonated with chlorosulfonic acid, according to Example 4, to the disulfonic acid intermediate. Neutralization of the acid with sodium hydroxide yields the disodium 2,6-bis (nonyloxy) naphthalene disulfonate.

The plaque barrier oral compositions of this invention may comprise any conventional pharmaceutically acceptable oral hygiene formulation that contains (and is compatible with) an effective amount of a plaque barrier agent as defined herein. Such formulations include, for example, mouthwashes, rinses, irrigating solutions, abrasive and nonabrasive gel dentifrices, denture cleansers, coated dental floss and interdental stimulator coatings, chewing gums, lozenges, breath fresheners, foams and sprays.

The plaque barrier agents may be present in these formulations in effective concentrations generally in the range of from about 0.05 weight percent to as much as 30 weight percent or the limit of compatibility with the vehicle. However, no advantage will be derived from concentrations in excess of about 20 weight percent. A preferred concentration range for the plaque barrier agents in the formulations of the invention is from about 0.5 to about 10 weight percent. A more preferred range is from about 2 to about 8 percent by weight, about 5% being the presently most preferred concentration in a nonabrasive gel vehicle.

The pH of these plaque barrier preparations should be between pH 5.0 and 10.0, preferably between pH 5.0 and 8.0, more preferably between about pH 6.0 and 7.5. Lower pH than 5.0 is undesirable because of the possible enhancement of enamel demineralization.

Suitable conventional pharmaceutically acceptable vehicles that can be employed with the plaque barrier agents to prepare the barrier compositions of this invention may comprise water, ethanol; such humectants as polypropylene glycol, glycerol and sorbitol; such gelling agents as cellulose derivatives, for example, Methocel, carboxymethylcellulose (CMC 7MF) and Klucel HF, polyoxypropylene/polyoxyethylene block copolymers, for example, Pluronic F-127, Pluronic F-108, Pluronic P-103, Pluronic P-104, Pluronic P-105, and Pluronic P-123, colloidal magnesium aluminosilicate complexes such as Veegum, and mucoprotein thickening agents such as Carbopol 934; gel stabilizers such as the silicon dioxides, for example, Cab-O-Sil M5, and polyvinylpyrrolidone; sweeteners such as sodium saccharin; preservatives such as citric acid, sodium benzoate, cetylpyridinium chloride, potassium sorbate, methyl and ethyl parabens; detergents such as sodium lauryl sulfate, sodium cocomonoglyceride sulfonate, sodium lauryl sarcosinate and polyoxyethylene isohexadecyl ether (Arlasolve 200) and approved colors and flavors.

The following specific examples will serve further to illustrate the plaque barrier compositions of this invention.

EXAMPLE A—Mouthwash Solution

| Barrier Agent | 0.5-2.0% w/w |
|---|---|
| Glycerol (humectant) | 6.0 |
| Pluronic F-108 | 1.0 |
| Sodium saccharin (sweetener) | 0.3 |
| Deionized Water | q.s. |
| Flavors | 1.0 |
| | 100.0 |

EXAMPLE B—Mouthwash Solution

| Plaque Barrier Agent | 0.5-3.0% w/w |
|---|---|
| Ethanol, USP | 15.0 |
| Pluronic F-108 (foaming agent) | 2.0 |
| Glycerol (humectant) | 10.0 |
| Sorbitol (humectant) | 10.0 |
| Sodium saccharin (sweetener) | 0.2 |
| Deionized Water | q.s. |
| Flavors | 0.2 |
| | 100.0 |

EXAMPLE C—Abrasive Dentrifice Gel

| Plaque Barrier Agent | 2.0-10.0% w/w |
|---|---|
| Fumed Silica (abrasive) | 55.0 |
| Sodium Lauryl Sulfate (detergent) | 1.5 |
| Glycerol (humectant) | 10.0 |
| Carboxymethylcellulose (gelling agent) | 2.0 |
| Sodium saccharin (sweetener) | 0.2 |
| Sorbitol (humectant) | 10.0 |
| Flavors | 1.0 |
| Deionized Water | q.s. |
| Preservative | 0.05 |
| | 100.0 |

EXAMPLE D—Chewing Gum

| Plaque Barrier Agent | 1.0-11.0% w/w |
|---|---|
| Gum Base | 21.3 |
| Sugar | 48.5-58.5 |
| Corn Syrup (Baume 45) | 18.2 |
| Flavors | 1.0 |
| | 100.0 |

EXAMPLE E—Nonabrasive Gel Dentifrice

| Plaque Barrier Agent | 0.05-30.0% w/w |
|---|---|
| Sorbistat (preservative) | 0.15 |
| Deionized Water | q.s. |
| Silicon Dioxide (gel stabilizer) | 1.0 |
| Pluronic F-127 (gelling agent) | 20.0 |
| Sodium Saccharin | 0.2 |
| Flavors | 1.5 |
| | 100.0 |

EXAMPLE F

The following formulation illustrates a presently preferred nonabrasive gel composition containing a barrier agent in accordance with the present invention.

| Ingredients | % w/w | |
|---|---|---|
| Distilled Water | q.s. | |
| Sodium Saccharin (sweetener) | 0.20 | |
| Sodium Benzoate (preservative) | 0.30 | |
| FD&C Blue #1 (0.1% aq. soln.) | 0.27 | |
| D&C Yellow #10 (0.5% aq. soln.) | 0.50 | |
| Gelling agent | 18.00 | |
| Glycerol (Humectant) | 20.00 | |
| Cab-O-Sil M5 (Silicon Dioxide) | 1.00 | |
| Plaque Barrier Agent | 5.00 | (dry basis) |
| Flavor | 0.80 | |
| | 100.0 | |

While the details of preparing all of the above formulations are well within the skill of the art, a suggested procedure for preparing the gel formulation of this example will be described for completeness.

In a first container the water, sodium saccharin, sodium benzoate and dyes are mixed. Then the container is put into an ice bath. When the temperature reaches 6° C., the gelling agent is added and the contents mixed slowly until the gelling agent is dissolved. Then the solution is heated to 70° C.

Into a second container is added the glycerin. Then the Cab-O-Sil M5 is sprinkled in with mixing. Then the plaque barrier agent is added and mixing continued to a smooth paste. The paste is then heated in a water bath with mixing to a temperature of 70° C.

The contents of the first container are added to the second container and blended together until the batch is homogenous while maintaining a 70° C. temperature. Then the flavoring is added, all mixing is stopped, and the formulation allowed to settle for approximately one hour. If necessary to remove air bubbles, overnight refrigeration may be employed.

These compositions are preferably employed from one to three times daily in a routine oral hygiene program to prevent the attachment of plaque to the teeth.

Variations can, of course, be made without departing from the spirit or scope of the invention.

I claim:

1. An alkoxynaphthalene sulfonic acid compound having a structure selected from the group consisting of structure (A),

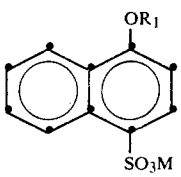

(A)

structure (B),

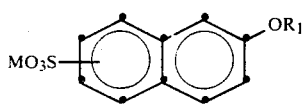

(B)

and structure (C),

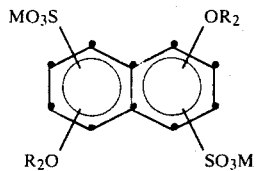

(C)

wherein $R_1$ is a linear or branched alkyl having 6 to 20 carbon atoms, $R_2$ is a linear or branched alkyl having 8 to 20 carbon atoms, and M is selected from the group consisting of hydrogen, lithium, sodium, potassium, calcium, magnesium, zinc, aluminum, ammonium and the substituted ammonium ions derived from pharmaceutically acceptable organic amines.

2. An oral hygiene composition comprising a therapeutically effective amount for preventing deposition of dental plaque on teeth of an alkoxynaphthalene sulfonic acid compound having a structure selected from the group consisting of structure (A),

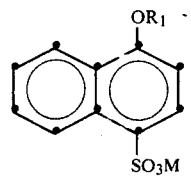

(A)

and structure (B),

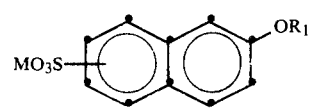

(B)

and structure (C),

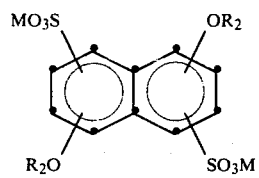

(C)

wherein $R_1$ is a linear or branched alkyl having 6 to 20 carbon atoms, $R_2$ is a linear or branched alkyl having 8 to 20 carbon atoms, and M is selected from the group consisting of lithium, sodium, potassium, calcium, magnesium, zinc, aluminum, hydrogen, ammonium, and substituted ammonium ions derived from pharmaceutically acceptable organic amines, in a pharmaceutically acceptable oral hygiene vehicle compatible with said polymer.

3. The composition of claim 2 wherein M is a metal selected from the group consisting of potassium, lithium, sodium, calcium, magnesium, zinc and aluminum.

4. A method of preventing deposition of dental plaque on teeth comprising periodically applying to the teeth a composition of claim 2.

5. The method of claim 4 wherein said composition is applied from about 1 to about 3 times per day.

6. The composition of claim 2 in the form of an oral hygiene formulation selected from the group consisting of mouthwashes, mouthrinses, irrigating solutions, abrasive gel dentifrices, non-abrasive gel dentifrices, denture cleansers, coated dental floss, coated interdental stimulators, chewing gums, lozenges, breath fresheners, foams and sprays.

* * * * *